United States Patent
Grotz

(10) Patent No.: US 7,722,674 B1
(45) Date of Patent: May 25, 2010

(54) LINEARLY EXPANDING SPINE CAGE FOR ENHANCED SPINAL FUSION

(75) Inventor: R. Thomas Grotz, San Francisco, CA (US)

(73) Assignee: Innvotec Surgical Inc., Brisbane, CA (US)

(*) Notice: Subject to any disclaimer, the term of this patent is extended or adjusted under 35 U.S.C. 154(b) by 279 days.

(21) Appl. No.: 11/202,725

(22) Filed: Aug. 12, 2005

(51) Int. Cl.
*A61F 2/44* (2006.01)

(52) U.S. Cl. .................................................. 623/17.11

(58) Field of Classification Search ... 623/17.11–17.16; 606/90
See application file for complete search history.

(56) References Cited

U.S. PATENT DOCUMENTS

| | | | |
|---|---|---|---|
| 3,875,595 A | 4/1975 | Froning | |
| 4,863,476 A * | 9/1989 | Shepperd | 623/17.15 |
| 4,932,975 A | 6/1990 | Main et al. | |
| 5,236,460 A | 8/1993 | Barber | |
| 5,609,636 A * | 3/1997 | Kohrs et al. | 623/17.16 |
| 5,653,763 A | 8/1997 | Errico et al. | |
| 5,665,122 A | 9/1997 | Kambin | |
| 5,980,522 A * | 11/1999 | Koros et al. | 623/17.11 |
| 6,039,761 A | 3/2000 | Li et al. | |
| 6,102,950 A * | 8/2000 | Vaccaro | 623/17.16 |
| 6,127,597 A | 10/2000 | Beyar et al. | |
| 6,371,989 B1 * | 4/2002 | Chauvin et al. | 623/17.11 |
| 6,375,682 B1 | 4/2002 | Fleischmann et al. | |
| 6,395,032 B1 | 5/2002 | Gauchet | |
| 6,409,766 B1 | 6/2002 | Brett | |
| 6,436,140 B1 | 8/2002 | Liu et al. | |
| 6,454,806 B1 | 9/2002 | Cohen et al. | |
| 6,500,205 B1 | 12/2002 | Michelson | |
| 6,652,584 B2 | 11/2003 | Michelson | |
| 6,666,891 B2 | 12/2003 | Boehm, Jr. et al. | |
| 6,709,458 B2 | 3/2004 | Michelson | |

(Continued)

FOREIGN PATENT DOCUMENTS

EP 1290985 A2 3/2003

(Continued)

OTHER PUBLICATIONS

"Wedge." Encarta World English Dictionary, North American Edition [online], [retrieved on Sep. 6, 2007]. Retrieved from the Internet <URL: http://encarta.msn.com>.*

(Continued)

*Primary Examiner*—Pedro Philogene
(74) *Attorney, Agent, or Firm*—Downs Rachlin Martin PLLC

(57) ABSTRACT

A linearly expanding spine cage has a minimized diameter in its unexpanded state that is equal to the diameter of an insertion groove cut into adjacent vertebral bodies. The cage conformably engages between the endplates of adjacent vertebrae to effectively distract the disc space, widen neuroforamina, stabilize the motion segments and eliminate pathologic spine motion. Angular deformities can be corrected, and natural curvatures maintained. The cage enhances spinal arthrodesis by creating a rigid spine segment. Expanding linearly (vertically, along the vertical axis of the adjacent spine) rather than uniformly, the cage height increases and holds the vertebrae with fixation forces greater than adjacent bone and soft tissue failure forces. Stability is thus achieved immediately, enabling patient function by eliminating painful motion. The cage width remains stable, so as to decrease impingement upon a second cage, or upon soft tissue structures in the immediate vicinity, including neural or vascular elements.

14 Claims, 12 Drawing Sheets

U.S. PATENT DOCUMENTS

| | | | |
|---|---|---|---|
| 6,716,247 | B2 | 4/2004 | Michelson |
| 6,719,796 | B2 | 4/2004 | Cohen et al. |
| 6,723,126 | B1 | 4/2004 | Berry |
| 6,764,491 | B2 | 7/2004 | Frey et al. |
| 6,793,679 | B2 | 9/2004 | Michelson |
| 6,814,756 | B1 | 11/2004 | Michelson |
| 6,821,298 | B1 | 11/2004 | Jackson |
| 6,835,206 | B2 | 12/2004 | Jackson |
| 6,893,464 | B2 | 5/2005 | Kiester |
| 6,962,606 | B2 | 11/2005 | Michelson |
| 6,972,035 | B2 | 12/2005 | Michelson |
| 6,981,989 | B1 | 1/2006 | Fleischmann et al. |
| 7,001,431 | B2 | 2/2006 | Bao et al. |
| 7,018,416 | B2 | 3/2006 | Hanson et al. |
| 7,056,343 | B2 | 6/2006 | Schäfer |
| 7,060,073 | B2 | 6/2006 | Frey et al. |
| 7,118,598 | B2 | 10/2006 | Michelson |
| 7,128,760 | B2 | 10/2006 | Michelson |
| 7,204,853 | B2 | 4/2007 | Gordon et al. |
| 7,211,112 | B2 * | 5/2007 | Baynham et al. .......... 623/17.11 |
| 7,214,243 | B2 * | 5/2007 | Taylor ..................... 623/17.11 |
| 7,217,293 | B2 | 5/2007 | Branch, Jr. |
| 7,282,063 | B2 | 10/2007 | Cohen et al. |
| 7,291,150 | B2 | 11/2007 | Graf |
| 7,291,158 | B2 | 11/2007 | Crow et al. |
| 7,316,686 | B2 | 1/2008 | Dorchak et al. |
| 7,316,714 | B2 | 1/2008 | Gordon et al. |
| 7,326,248 | B2 | 2/2008 | Michelson |
| 7,351,261 | B2 | 4/2008 | Casey |
| 7,410,501 | B2 | 8/2008 | Michelson |
| 2002/0138146 | A1 * | 9/2002 | Jackson ................... 623/17.15 |
| 2005/0043800 | A1 | 2/2005 | Paul et al. |
| 2005/0216084 | A1 | 9/2005 | Fleischmann et al. |
| 2005/0229433 | A1 | 10/2005 | Cachia |
| 2006/0167547 | A1 * | 7/2006 | Suddaby ................... 623/17.11 |
| 2006/0264968 | A1 | 11/2006 | Frey et al. |
| 2007/0050030 | A1 | 3/2007 | Kim |
| 2007/0093901 | A1 | 4/2007 | Grotz et al. |
| 2007/0179611 | A1 | 8/2007 | DiPoto et al. |
| 2007/0233254 | A1 | 10/2007 | Grotz et al. |
| 2007/0255413 | A1 | 11/2007 | Edie et al. |
| 2007/0255415 | A1 | 11/2007 | Edie et al. |
| 2008/0058930 | A1 | 3/2008 | Edie et al. |
| 2008/0188941 | A1 | 8/2008 | Grotz |

FOREIGN PATENT DOCUMENTS

| | | |
|---|---|---|
| WO | 0209626 A | 2/2002 |
| WO | 0238062 A2 | 5/2002 |
| WO | 2004016205 A2 | 2/2004 |
| WO | 2004019829 A | 3/2004 |
| WO | 2007022021 A1 | 2/2007 |
| WO | WO 2008/011371 | 1/2008 |

OTHER PUBLICATIONS

International Search Report and Written Opinion dated Jan. 3, 2007 regarding related PCT/US2006/031528 filed Aug. 11, 2006, Thomas R. Grotz.

International Search Report and Written Opinion dated Jun. 5, 2009, regarding PCT/US2009/000974 filed Feb. 17, 2009.

* cited by examiner

LINEARLY EXPANDING SPINE CAGE FOR ENHANCED SPINAL FUSION

BACKGROUND

Field of the Invention

The field of the invention relates to medical devices for stabilizing the vertebral motion segment. More particularly, the field of the invention relates to a device, a linearly expanding spine cage (LEC), and a method for providing improved spinal intervertebral body distraction and fusion.

Inability to Expand and Distract Endplates

Referring to FIG. 1, a conventional spine cage or implant 101 is characterized by a cylindrical body comprising a plurality of threads 104 provided on the exterior surface for contact with adjacent vertebral segments or endplates 102a and 102b, which are shown as blocks for clarity. Conventional spine cage 101 is typically inserted in tandem between vertebral segments 102a and 102b.

Such existing devices for interbody stabilization, such as conventional spine cage or implant 101, have important and significant limitations. These limitations include an inability to expand and distract the endplates. Separation of the endplates serves to create lordosis within the spine. Current devices for interbody stabilization include static spacers composed of titanium, PEEK, a high performance thermoplastic polymer produced by VICTREX, (Victrex USA Inc., 3A Caledon Court; Greenville, S.C. 29615), carbon fiber, or resorbable polymers. Current interbody spacers do not improve interbody lordosis and can contribute to the formation of a kyphotic segment and the clinical problem of "flatback syndrome." Separation of the endplates increases space available for the neural elements, specifically the neural foramen. Existing static cages do not reliably improve space for the neural elements. Therefore, what is needed is an expanding cage that will increase space for neural elements centrally and in the neural foramen.

Poor Interface Between Bone and Biomaterial

Another problem with conventional devices for interbody stabilization includes poor interface between bone and biomaterial. Conventional static interbody spacers form a weak interface between bone and biomaterial. Although the surface of such implants is typically provided with a series of circumferential threads or grooves 104, such threads are uniform and are in parallel with applied horizontal vectors or side to side motion. That is, the threads offer no resistance to movement applied to either side 106 of the endplates (as opposed to force applied to the front or back Thus, nonunion is common in allograft, titanium and polymer spacers, due to motion between the implant and host bone. Conventional devices typically do not expand between adjacent vertebrae.

Therefore, what is needed is a way to expand an implant to develop immediate fixation forces that can exceed the ultimate strength at healing. Such an expandable implant ideally will maximize stability of the interface and enhance stable fixation. The immediate fixation of such an expandable interbody implant advantageously will provide stability that is similar to that achieved at the time of healing. Such an implant would have valuable implications in enhancing early post-operative rehabilitation for the patient.

Large Diameter Devices Require Wide Exposure of Neural Structures

Another problem of conventional interbody spacers is their large diameter requiring wide exposure. Existing devices used for interbody spacers include structural allograft, threaded cages, cylindrical cages, and boomerang-shaped cages. Conventional devices have significant limitation with regard to safety and efficacy. Regarding safety of the interbody spacers, injury to neural elements may occur with placement from an anterior or posterior approach. A conventional spine cage lacks the ability to expand linearly in a vertical direction without also changing position or expanding laterally, thus working against stable fixation.

The risks to neural elements are primarily due to the disparity between the large size of the cage required to adequately support the interbody space, and the small space available for insertion of the device, especially when placed from a posterior or transforminal approach. Existing cylindrical interbody implants are characterized by a width that is equal to their height. Therefore, implantation requires a wide exposure and potential compromise of vascular and neural structures. Given the proximity of nerve roots and vascular structures to the insertion site, and the solid, relatively large size of conventional hollow devices, such constraints predispose a patient to foraminal (nerve passage site) violation, and possible neural and vascular injury.

Therefore, what is needed is an expanding spine cage that is capable of insertion with minimal invasion into a smaller aperture. Such a minimally sized spine cage advantageously could be expanded by instrumental force application. Due to the small size of the cage, the nerves can be anatomically separated from the cage proximity, thus allowing a greater level of safety during the surgical procedure. Such an expandable implant would permit a more narrow exposure in the space outside of the vertebral body, with expansion inside of the interbody space.

What is also needed is a smaller expanding spine cage that is easier to operatively insert in a patient with minimized trauma in contrast to conventional, relatively large devices that create needless trauma to nerve roots in the confined space of the vertebral region.

Limited Capacity for Interbody Bone Formation

Existing interbody implants have limited space available for bone graft. Adequate bone graft or bone graft substitute is critical for a solid interbody arthrodesis. It would be desirable to provide an expandable interbody cage will provide a large volume of bone graft material to be placed within the interbody space. Additionally, conventional interbody implants lack the ability to stabilize endplates completely and prevent them from moving. Therefore, what is also needed is an expanding spine cage wherein the vertebral endplates are subject to forces that both distract them apart, and hold them from moving. Such an interbody cage would be capable of stabilization of the motion segment, thereby reducing micromotion, and discouraging pseudo arthrosis (incomplete fusion) and pain.

Ideally, what is needed is a spine cage or implant that is capable of increasing its expansion diameter to a calculated degree. Such a spine cage would permit restoration of normal spinal alignment after surgery and hold the spine segments together rigidly, mechanically, until healing occurs. What is also needed is an expanding cage or implant that is capable of holding vertebral or joint sections with increased pullout strength to minimize the chance of implant subsidence in the healing period.

It would also be desirable if such a cage could expand linearly (vertically, along the vertical axis of the entire spine) rather than uniformly which would take up more space inside the vertebral body surfaces.

SUMMARY

An aspect of the invention comprises a linearly expanding spine cage (LEC) comprising two halves joined along a common longitudinal axis to form a cylinder with a minimized diameter in its unexpanded state that is equal to the diameter of an insertion groove cut in adjacent vertebral bodies. The LEC is thus conformably engaged between the endplates of adjacent vertebra to effectively distract the intervertebral area, restore space for neural elements, stabilize the motion segment and eliminate pathologic segmental motion. The LEC enhances spinal arthrodesis by creating a rigid spine segment.

The LEC provides a significant advantage by enabling a comparatively large quantity of bone growth enhancing agents to be contained within its interior and communicated directly to adjacent bone over a maximized surface area due to a perforated design with apertures dispersed through multiple rows of corrugations, ridges, points, troughs or other features for bone engagement provided on radial surfaces of LEC halves. Importantly, this results in fixation forces greater than adjacent bone and soft tissue failure forces.

By expanding linearly (vertically, along the vertical axis of the entire spine) rather than uniformly (which would take up more space inside the vertebral body surfaces), the cage height increases to hold the vertebrae, while the width remains stable so as to decrease impingement upon a second cage, or upon soft tissue structures in the immediate vicinity (neural elements).

Generally, two LECs are used for fusion through the anterior approach—though the surgeon can choose any insertional vector. The cages may be inserted in parallel, or obliquely to accommodate located anatomy, and to adjust deformities such as scoliosis, kyphosis, and spondylolisthesis.

The clinical goals of the LEC and method for its insertion reduce pain, improve function, and permit early mobilization of the patient after fusion surgery. Since the LEC pullout forces are greater than vertebral body failure forces, patients can mobilize more quickly than was previously possible. Once healing (fusion or arthrodesis) does occur, the implants become incorporated and their role becomes quiescent.

The present LEC provides more internal to external graft bone space exposure, easier insertion, less risk of insertional damage to nerve roots and other tissue, and thus a substantially improved immediate and long term result. The specialized exterior on the outside of the LEC seeks to balance multiple projections, tines, or other bone engaging features that will hold firmly adjacent bone to prevent prosthetic extrusion, while being sufficiently rounded so as to avoid injuring nearby nerve or vascular structures. Bone ingrowth is encouraged by the perforated design of the LEC and the exterior corrugations that greatly increase the surface area of the LEC that conformably engages adjacent vertebral bone. By avoiding a square or rectangular configuration, the LEC is less prone toward subsidence.

BRIEF DESCRIPTION OF THE DRAWINGS

The drawings are heuristic for clarity. The foregoing and other features, aspects and advantages of the invention will become better understood with reference to the following descriptions, appended claims and accompanying drawings in which:

FIG. 6B is a perspective view of the interior of a second half of the LEC of. FIG. 5 according to an aspect of the invention

DETAILED DESCRIPTION

Figure 1:
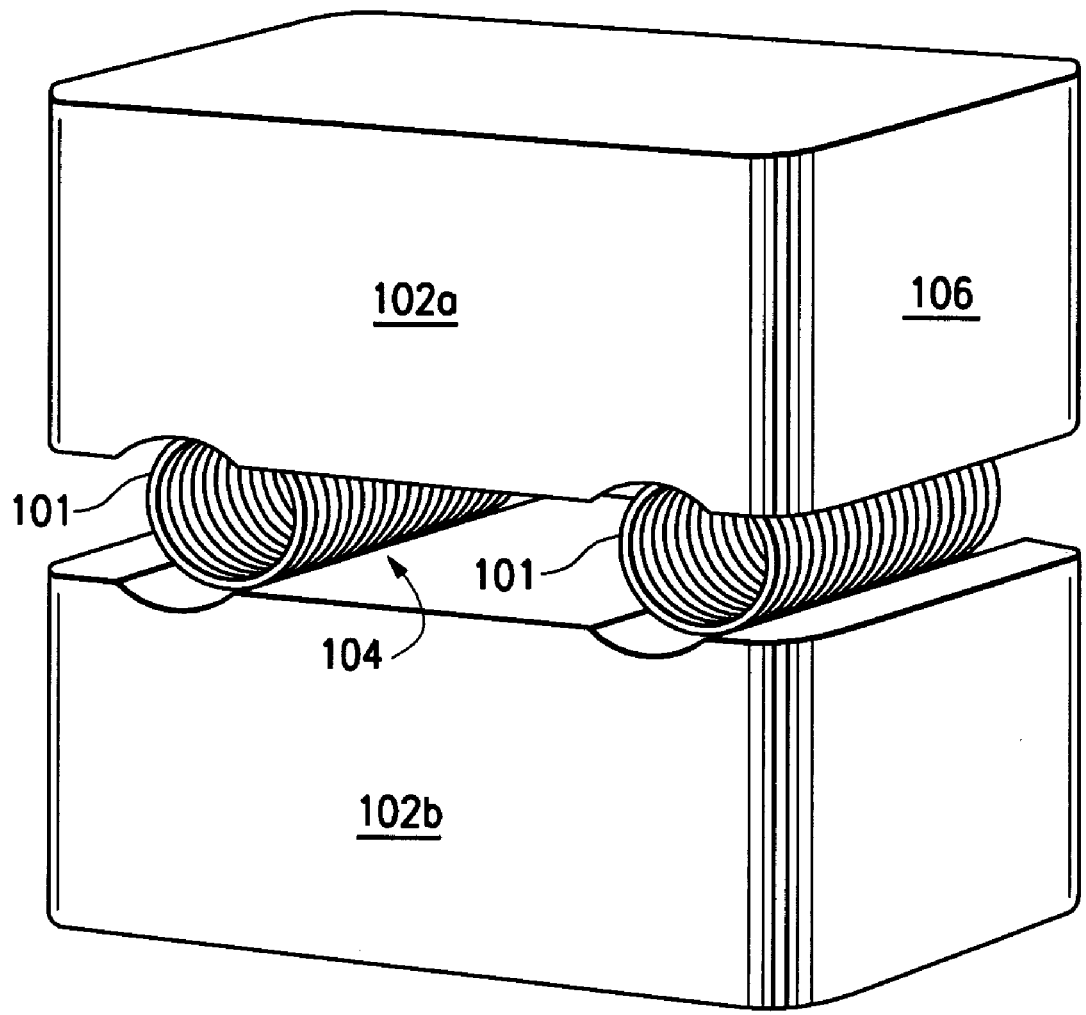
FIG. 1 is a perspective view of a conventional non-expanding cylindrical spine cage, resembling products in current use.
Figure 2:
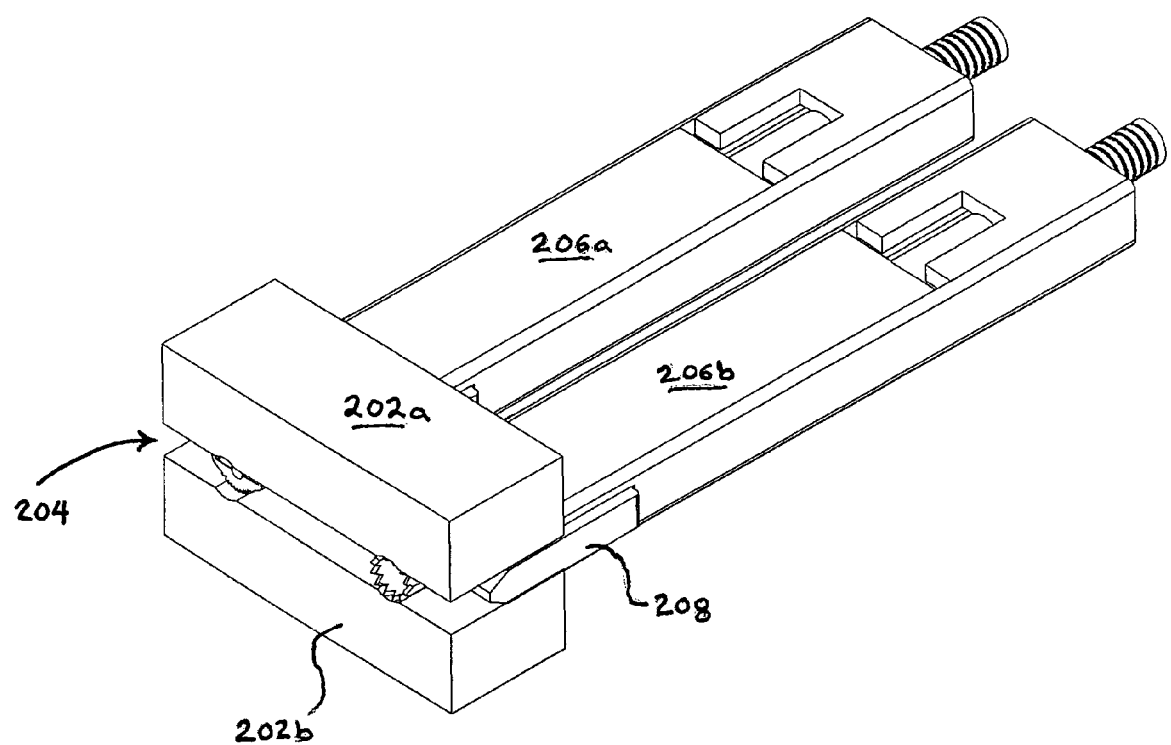
FIG. 2 is a perspective view of two cannulas inserted between vertebrae for placement of a spine cage and a cutting tool according to an aspect of the invention.

Referring to FIG. 2, vertebral segments 202a and 202b are shown with an 8 mm gap representing an average intervertebral space 204. The vertebral segments 202a and 202b are shown as blocks for clarity. A complete discectomy is performed prior to the insertion of the LEC.

As is well understood by one skilled in the art, the intervertebral disc occupying space 204 will be removed using standard techniques including rongeur, curettage, and endplate preparation to bleeding subchondral bone. The posterior longitudinal ligament will be divided to permit expansion of the intervertebral space.

The intervertebral space 204 will be distracted to 10 mm using a rotating spatula (Not shown. This is a device that looks like a wide screw driver that can be placed into the disc space horizontally and turned 90 degrees to separate the endplates).

Referring to FIG. 2 through FIG. 5, one or two 10 mm cage cannulas 206 are inserted between the vertebral segments 202a and 202b. It will be appreciated that the present cannulas can be made smaller than conventional cannulas due to the expanding nature of the 10 mm spine cage and thereby minimize trauma to nerve roots in the spinal column. Each cannula has a fork 208 on the front end which is 10 mm tall. The fork properly levels the vertebrae for operation. Each cannula also has four spikes 210 which tap into the vertebrae above and below thereby preventing bone movement during the operation. For clarity, only the two top spikes are shown. Additional spikes may be added if needed.

It will be appreciated that the spiked tips 210 of the insertion cannulas advantageously stabilize the working surfaces of the vertebral segments to a high degree such that all bone movement and misalignment is substantially prevented during the operation. With a narrow cannula in place, the neural and vascular elements are protected and a safe working channel is created for endplate preparation and cage placement. Insertion of the cage follows tapping of the endplates, or vertebral segments.

Figure 3:
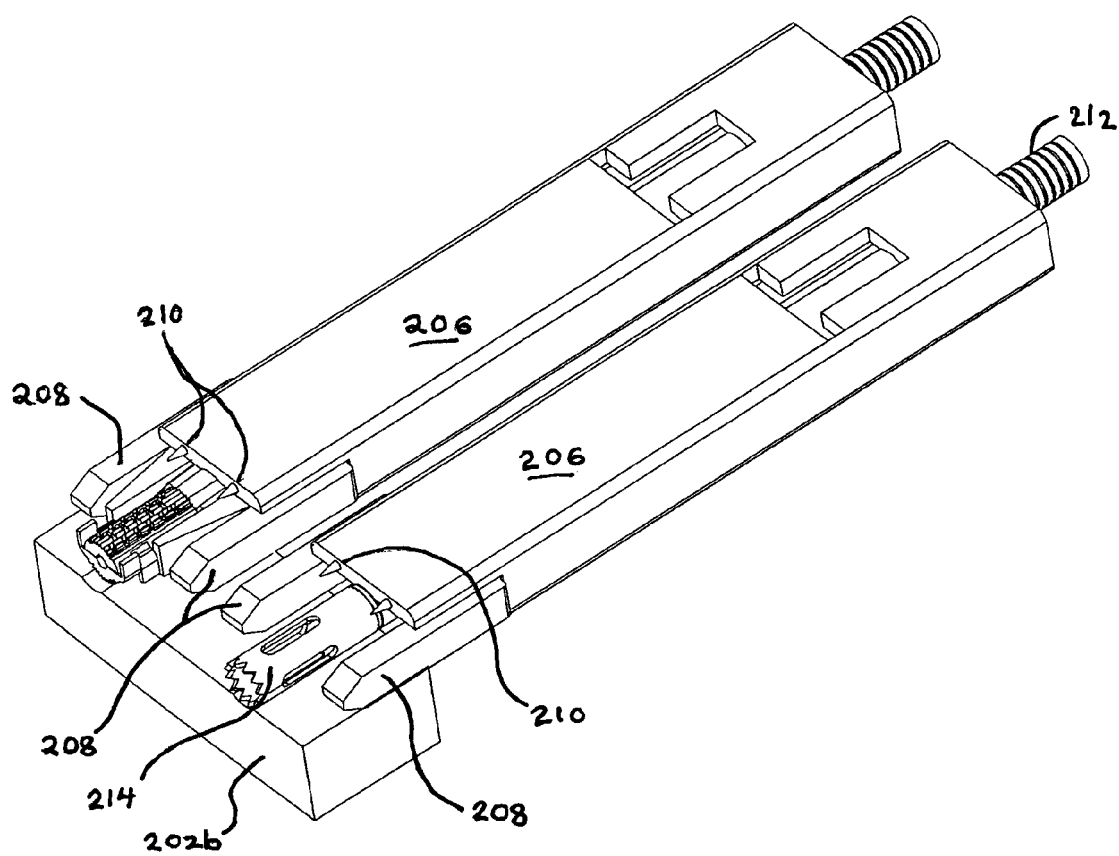
FIG. 3 is the perspective view of FIG. 2 with an upper vertebra removed for clarity.
Figure 4:
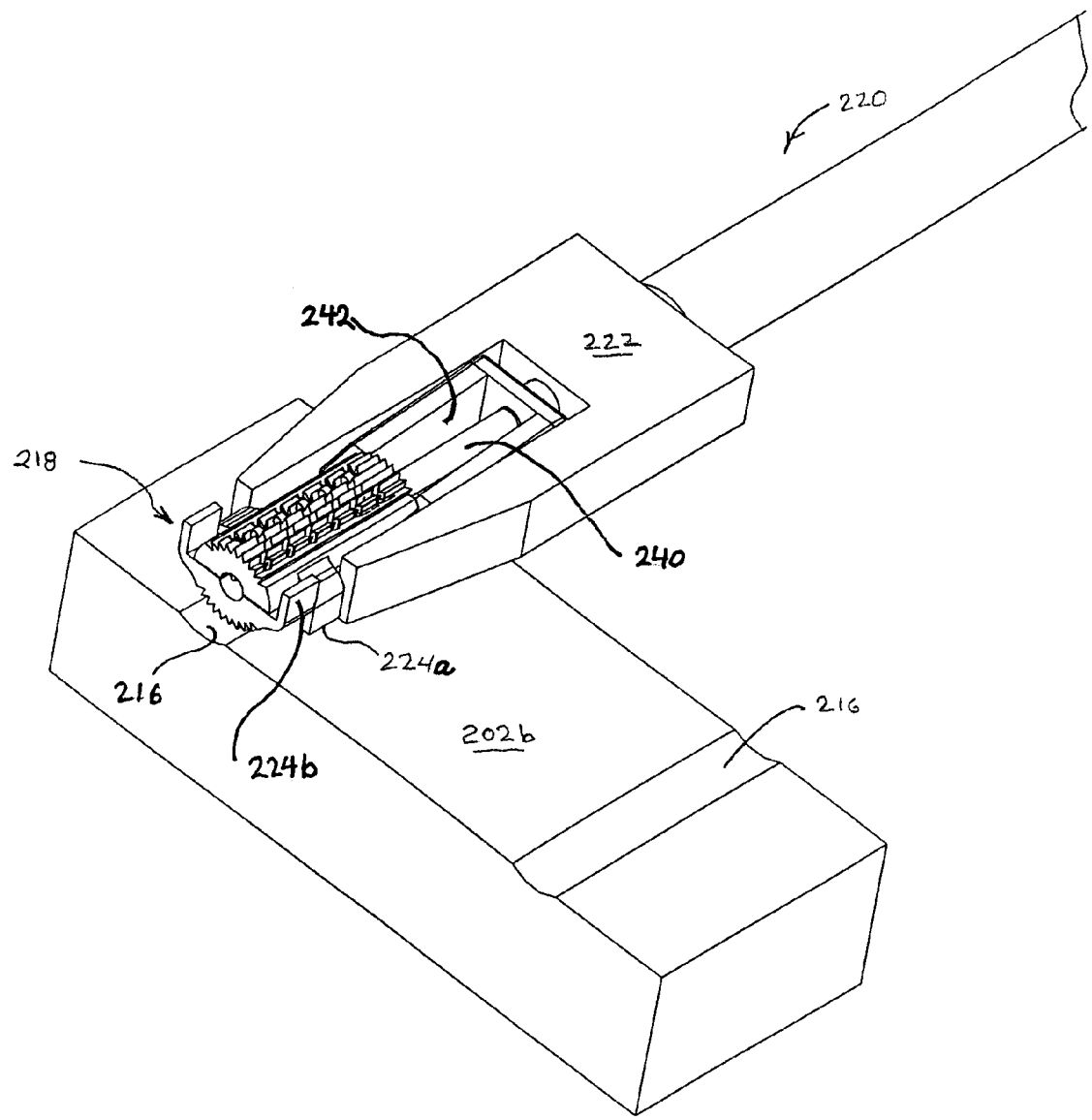
FIG. 4 is a perspective view of an insertion tool for positioning a spine cage between vertebrae according to an aspect of the invention.

Referring to FIG. 3 and FIG. 4, a 10 mm diameter motorized cutting tool 212 is inserted through a cannula. Cutting tool bit 214 is attached to the distal end of motorized cutting tool 212. The cutting bit is shaped like a hole saw which will cut and capture bone debris. This tool may not be necessary in the setting of an adequate discectomy. The non-cutting end of the cutting tool bit may be provided with a depth marking to indicate the depth of the cut. A limiter, such as a hard stop or "step off" can be added to prevent cutting too deeply.

Figure 5:
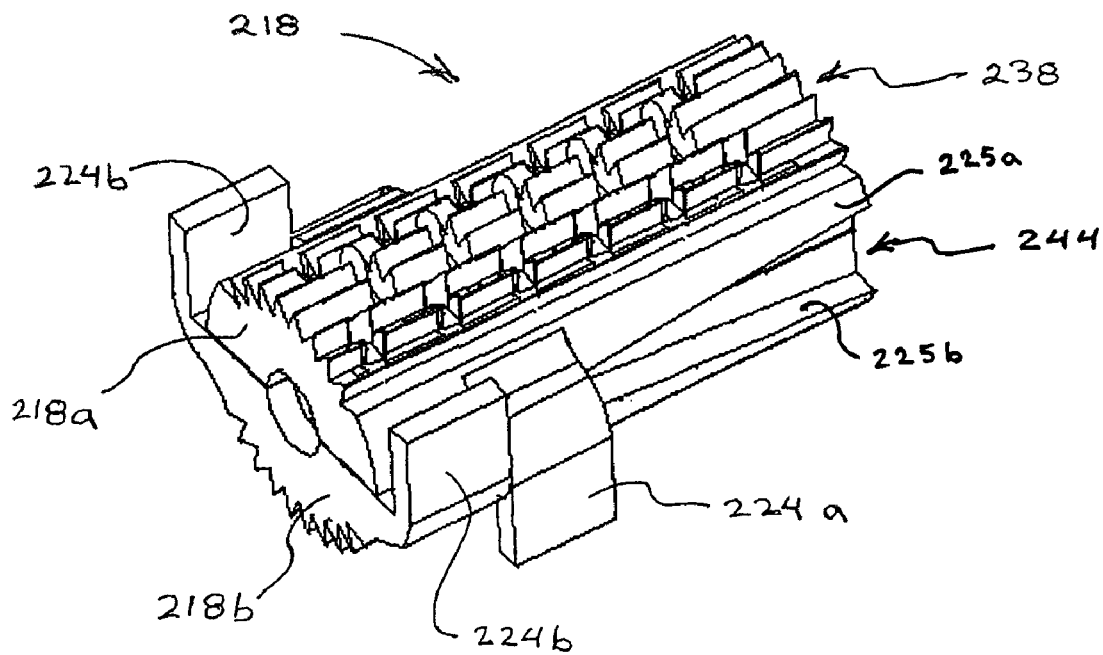
FIG. 5 is a perspective view of a linearly expanding spine cage (LEC) according to an aspect of the invention.

Once the cutting tool is removed, the vertebral surface will have a radial or rounded cut 216 acting as a base for stabilized, conformable receipt of a 10 mm diameter spine cage. FIG. 5 shows two such radial cuts or grooves 216 made by cutting tool 212 for placement of a spine cage. However, a tap with a fixed end point may be adequate to make a path for the cage to be inserted.

An important aspect of the invention is that the LEC cage 218 is, for example, only on average about 10 mm in width—the same diameter as the groove 216 made by cutting tool 212. This is critical because conventional cages are 14-16 mm high and wide, making them quite difficult to insert. Such conventional cages require large cannulas for insertion and subject nerve roots to trauma and injury. Mispositioning such a cage by as little as 3 mm can severely injure a nerve root.

In contrast, the present LEC cage can expand to a greater dimension without requiring so much space in insertion. As set forth above, this enables the present cannula to be much smaller than a conventional cannula. This safeguards the nerve roots and minimizes trauma. The 10 mm limitation is an example only. Thus, the cannula can be made as small as possible to take advantage of the unique expandable attributes of the LEC.

As will be explained in greater detail infra, the LEC can expand linearly to a vertical height by approximately 30-40 percent. The LEC is characterized by expansion ranges of, for example, from 7 mm up to 10 mm; from 9 mm up to 12 mm; or 12 mm up to about 16 mm. Due to the wide expansion range, a cannula advantageously can be as small as possible for insertion of the smaller LEC in its unexpanded state.

Referring to FIG. 4, an insertion tool 220 is provided in the cannula through its distal opening. The cannula in FIG. 4 has been removed for clarity. The insertion tool is provided with a fork end 222 that conformably holds, for example, a 10 mm LEC for insertion into precut groove 216.

It will be appreciated that the interior surface of the cannula advantageously matches or closely conforms to the exterior profile of the insertion tool and LEC, thereby properly orienting the LEC and preventing the LEC from rotating in the cannula. This further aids in precise placement of the LEC without injury to nearby nerve roots.

Referring to FIG. 4, as the insertion tool 220 is pushed toward the vertebrae 202b, the fork end 222 of the LEC insertion tool pushes on the wing sections 224a, 224b of the LEC cage thereby moving the LEC forward into position. Wing sections 224 act as a means for stabilizing and perfectly aligning the two halves of LEC 218 during the expansion process as will be explained infra. The wings of the LEC help to orient the LEC properly between the vertebrae. The insertion tool 220 also has depth markings 226 to indicate depth of insertion. A hard stop also can be added to prevent over travel.

Figure 6A:
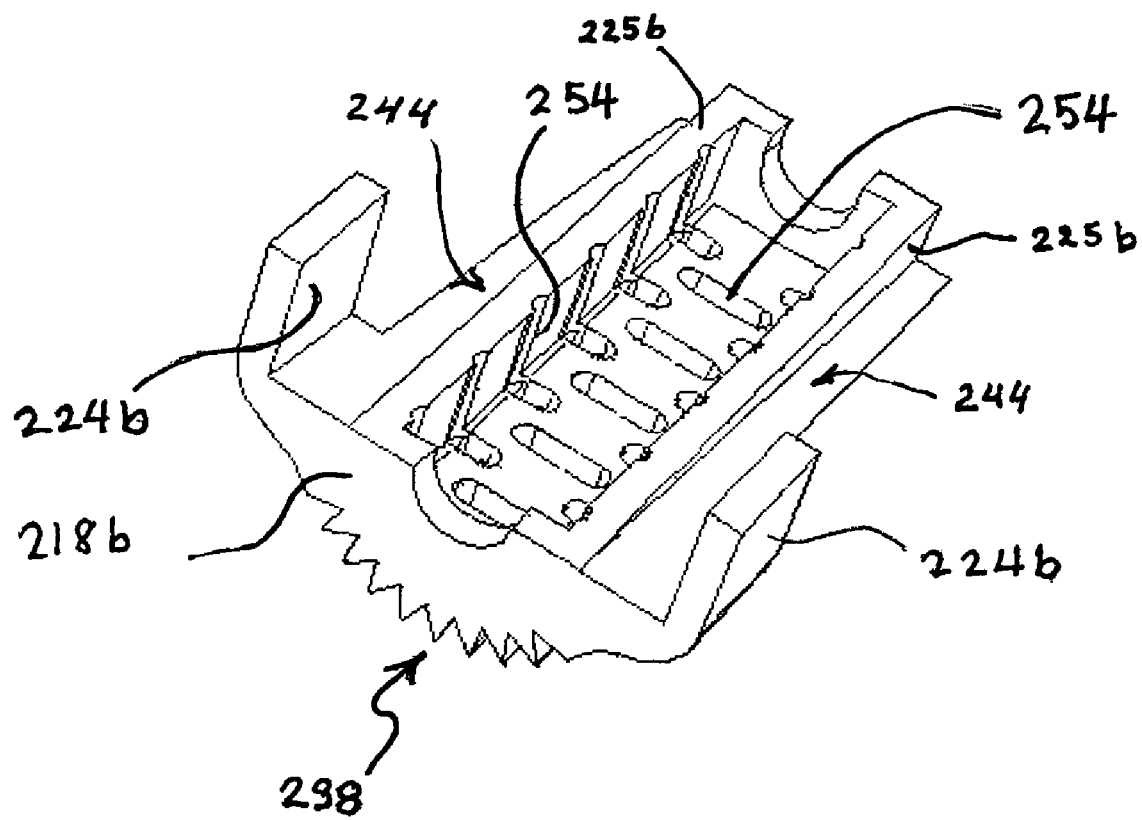
FIG. 6A is a perspective view of the interior of a first half of the LEC of FIG. 5 according to an aspect of the invention.
Figure 6B:
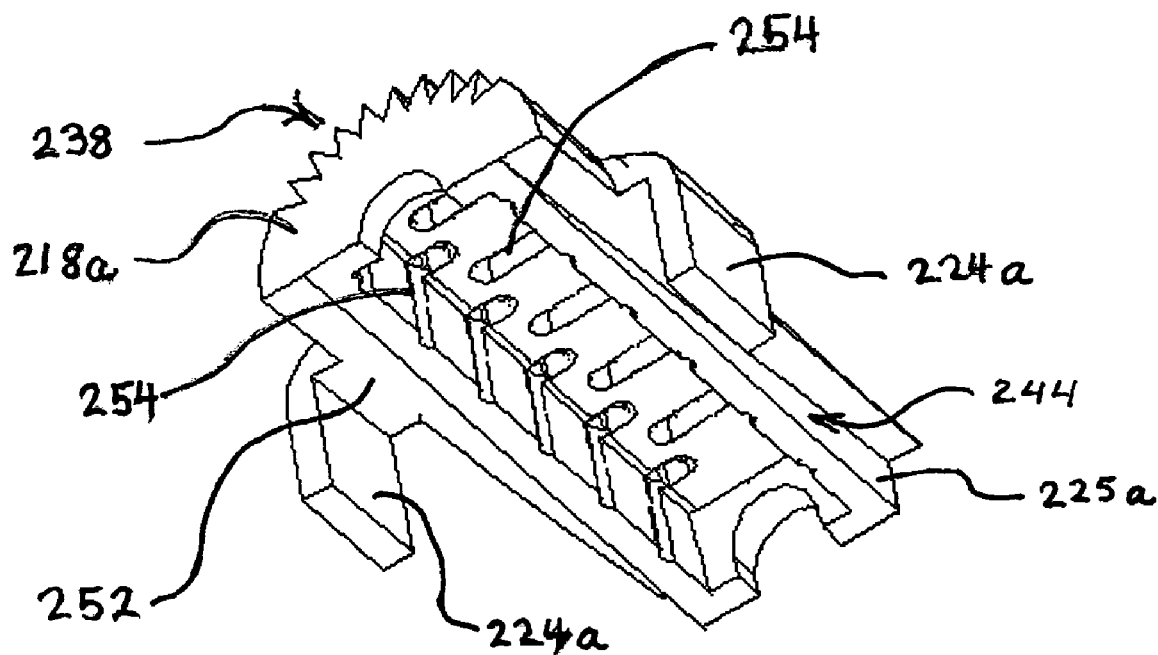

Referring to FIGS. 5, 6A, and 6B, it will be appreciated that cylindrical cage 218 comprises two halves, an upper half 218a and a lower half 218b wherein the radial surface of each upper and lower half conformably engages with the corresponding surface of radial cut 216 in each vertebral segment 202a and 202b. (202a is omitted for clarity) in which the LEC 218 is positioned. This is possible due to the minimized shape of the non-expanded spine cage which enables its radius to be substantially the same as that of cutting head 214 and cut or groove 216. This minimized diameter of the LEC further aids in precise placement of the LEC without injury to nearby nerve roots. Referring again to FIGS. 5, 6A, and 6B, each half 218a, 218b of the LEC 218 is provided with a series of parallel longitudinally extending ridges 238 disposed along the longitudinal axis of each bone contacting exterior surface of each LEC half 218a, 218b. These parallel longitudinal extending ridges are characterized by a substantially pyramidal cross section (see FIGS. 6A and 6B) and form multiple rows of rigid engagement surfaces providing strong frictional engagement against slippery bone surfaces, extending the length of the LEC. The parallel ridges are disposed orthogonally with respect to lateral or rotational forces applied to the vertebrae. Due to the plurality of the ridges and depth of their pyramidal cross sections, the ridges strongly resist applied rotational forces. The multiple engagement surfaces provided by the ridges 238 also effectively increase the surface area of the LEC 218 in contact with the radial groove 216 in the bone. The multiple engagement surfaces provided by the ridges 238 strongly lock the LEC in substantially invariant engagement with corresponding vertebral segments 102a and 102b by force from expansion of each LEC half with a corresponding vertebral body or segment.

It will be appreciated that providing other equivalent bone engaging features such as a multiplicity of pointed surfaces, corrugations or points extending over bone contacting surfaces of each LEC half 218a, 218b similarly provides a maximized surface area for bone engagement and fixation.

When seated in position, the surface configuration of the LEC prevents the LEC from rotating in the groove in the vertebral surface. This further enhances stable fixation of the LEC with the bone and prevents rollover and misalignment.

The cylindrical configuration of the LEC and matching radius of grooves 216 provide initially a 360° mating surface or bone to implant interface. This effectively doubles pullout forces with respect to the surface contact currently available in spinal reconstruction. Thus, the LEC is capable of withstanding at least 2000 Newtons (force pounds) in the perioperative period. In sitting, a person is capable of withstanding typically 1200 Newtons; when standing 800N, and when forward bending and heavy lifting up to 10,000N of intervertebral body force. Titanium is a preferential material for the LEC that achieves at least a 2000 Newton pullout force in the perioperative period.

The foregoing features enable the LEC to expand into the vertebrae with greater fixation forces than would be currently possible with known conventional devices. Thus, the requirements for additional stabilization procedures are reduced. This means that instead of achieving spine fusion by a series of conventional operative procedures, given the immediate solid fixation that accrues from the present LEC, operative procedures may be reduced in number, potentially to one operation. This advantageously would save the patient from pain, and the risks attendant with multiple anesthesias.

Due to the enhanced fixation and lateral stability, healing time is greatly reduced. Typically, once tissue is reconnected to bone, patients are only 30-40 percent healed after three-four weeks; 60-70 percent by six weeks; are 85 percent healed by 12 weeks; and 100 percent healed in about a year. This means, even though skin healing occurs, such superficial healing masks the long term need for joint immobilization to allow complete healing to occur. Such need for long-term immobilization has negative impacts on patients, their family, their employer, their livelihood and their future.

In contrast, the present LEC provides substantially immediate bone to implant fixation that is stabilized against rotational forces. This achieves an accelerated bone to implant fixation time without joint immobilization.

Due to the substantially immediate bone fixation, lateral stability and elimination of the need for immobilization, the LEC can be used for large animals; for example horses or large dogs such as 200 lb. mastiffs, which cannot follow instructions regarding limiting activities after injury and repair.

Once the LEC has been seated in position in radial groove 216, the cannula spikes 210 are removed from the vertebrae and the LEC is expanded. Pulling the cannula out slightly removes the spikes from the vertebrae and allows the vertebrae to be spread.

Referring to FIGS. 5, 6A and 6B, LEC 218 comprises an upper half cylinder 218a and a lower, complementary cylinder half 218b. The cylinder halves 218a, 218b are joined along a longitudinal axis to define a cylinder, the LEC, with an interior space for holding a quantity of bone growth enhancing agents as will be explained. Cylinder halves 218a, 218b also each comprise an integral, expansion alignment structure or generally U shaped wing 224a, 224b integrally formed with each respective LEC half. The upper wing 224a extends tangentially generally downward from the surface of the first cylindrical half 218a. The lower wing 224b extends upward from the radial surface of second cylindrical half 218b, immediately adjacent the first wing. During insertion, the wings form complementary U shaped end pieces that lock together the upper and lower portions 218a, 218b of the LEC, holding the LEC 218 together in the closed position while the LEC is inserted in its non expanded state into the substantially congruent groove 216 in a vertebral segment.

The complementary adjacent sides of the wings 224a, 224b slidably move against each other in opposite directions during expansion. The wings provide complementary contacting surfaces for equalizing force distribution in each respective LEC half such that the halves expand equally in opposite directions. The wings work cooperatively to control expansion in a linear direction and to maintain the alignment of respective halves of the cage during expansion process. When the LEC is in its fully expanded state, the wings cooperate to neutralize or block natural potentially deforming compression and shear forces. The wings thus provide controlled linear expansion of the two halves of the LEC and maintain each half in their predetermined alignment with the vertebral groove 216 during and after expansion.

Figure 7:
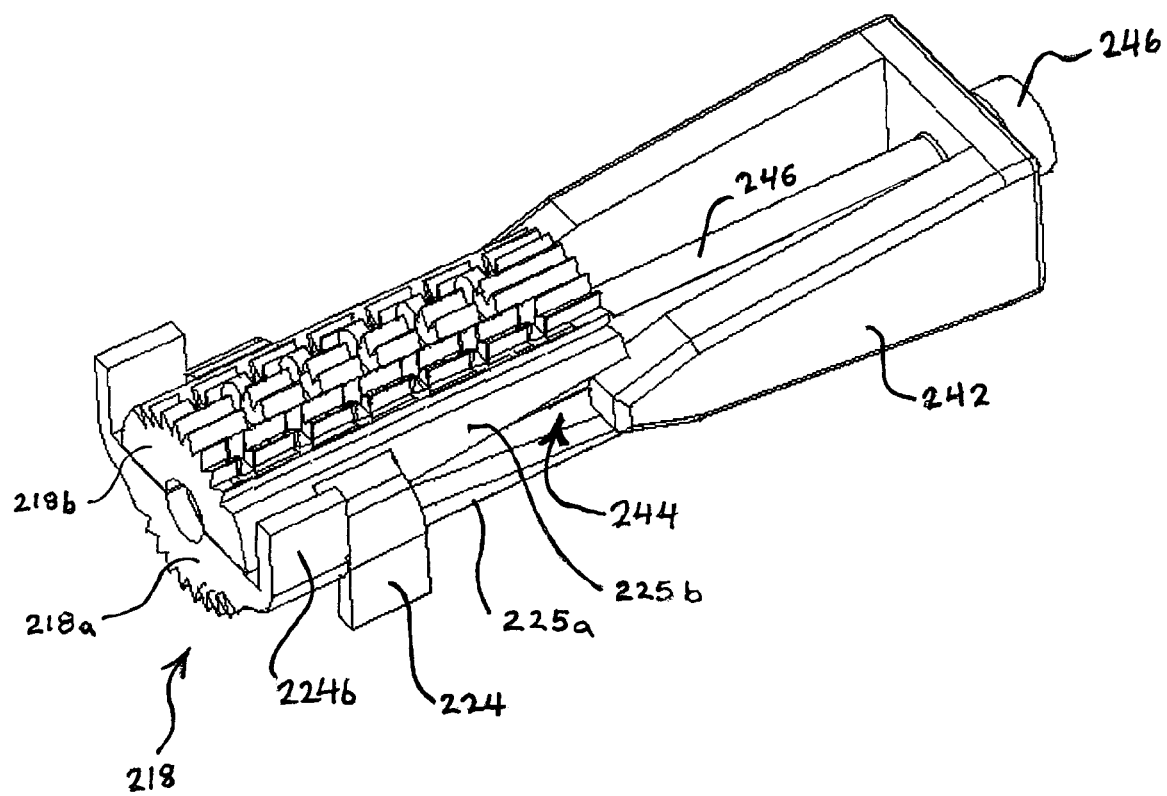
FIG. 7 is a perspective view of the LEC of FIG. 5 showing the expansion mechanism according to an aspect of the invention.

Referring to FIGS. 6A, 6B and 7 it is understood that the controlled expansion stabilization and alignment provided by the wings also is provided by side walls 225a, 225b that define expansion slot 244 in the sides of the LEC halves. Thus, the wings are optional. The expansion slot 244 in turn conformably receives the angled sides of expansion wedge 242. The sides or sidewalls 225a, 225b of the LEC halves 218a, 218b may be angled to form different dimensions for the expansion slot 244, into which the expansion wedge 242 advances. As the U shaped parallel sides of the expansion wedge 242 advance into the slot 244, they slide conformably against the sidewalls, holding the sidewalls of the LEC halves from both sides, thereby stabilizing the linear expansion of the LEC halves vertically.

Referring to FIGS. 4, 5, 7, 8 and 10C, the expansion mechanism is as follows. A rotary screwdriver or equivalent rotary driver 240 is inserted through an aperture in the center of the insertion tool 220 for making contact with an expansion means in the interior of the LEC 218. The distal end of the rotary driver makes contact with the head of a screw 246. Screw 246 operatively cooperates with nut 248 provided in the interior of the LEC. As the driver rotates the head of screw 246, the screw head 246 pushes against the base of expansion wedge 242. And, the wedged shaped, angled side portion 250 of expansion wedge 242 moves forward into a receiving slot 244. Receiving slot 244 is defined by the sides 225a, 225b of respective LEC halves 218a, 218b in the side of the cage 218.

Figure 8:
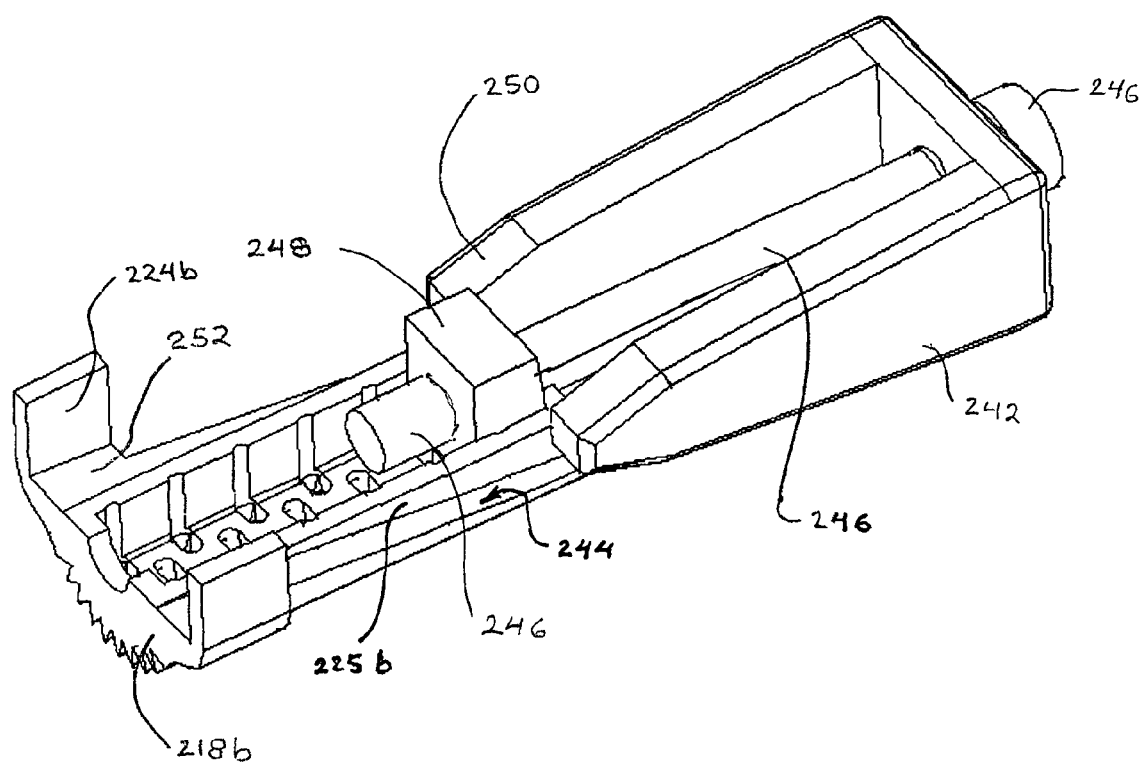
FIG. 8 is a perspective interior view of the LEC of FIG. 5 showing the expansion mechanism according to an aspect of the invention.

FIG. 8 shows a means for expanding the LEC linearly and generally orthogonally with respect to an axis of insertion. The exact angle of expansion can be predetermined by using an expansion wedge having a specific angle and height. Importantly, the expansion means also maintains the original diameter or radial dimension of each LEC half that remains in conformable contact with the bone, and thus does not interfere with the substantially immediate fixation achieved between the bone and multiple rows of corrugations or frictional engagement surfaces 238 provided on the radial surfaces of each LEC half 218a, 218b.

Means are provided for translating a rotary motion into a linear, vertical motion that expands the LEC vertically with respect to its axis of insertion, or at a desired angle determined by the angle of the expansion wedge to provide a full range of spinal correction. In FIG. 8 the expansion wedge 242 advances forward on an angled surface in expansion slot 244 defined by side walls 225b, 225a and provided on each side of the LEC. The forward movement of the expansion wedge simultaneously expands each cage half 218a, 218b at a predetermined angle, while maintaining the integrity of the sidewalls of the LEC during expansion for enclosing the bone growth enhancing material contained within the LEC. As the screw head 246 turns and pushes against the base of expansion wedge 242, the expansion wedge 242 moves forward into the receiving slot 244, and expands the halves of the cage 218 in a linear direction. The expansion wedge 242 moves all the way forward in the slot 244 and at the point of full expansion, comes to rest in a conformable end receiving space 252.

As will be explained further with reference to FIG. 10C, one of an assortment of expansion wedges having different angles and/or heights for the sides of the expansion wedge 242, may be selected for insertion into the slot 244 for imparting a full range of desired spinal correction. This is done by simply selecting an expansion wedge characterized by a desired height and angulation of one or both sides.

Thus, by turning the screwdriver, the expansion wedge 242 advances forward into the receiving slot 244 of the LEC 218 and the LEC expands linearly in a vertical direction at an angle predetermined by the angle and height of wedge 242. Once fully expanded, the ends of the expansion wedge 242 are trapped conformably within the receiving slot 244 and an end receiving space 252 defined by wings 224a, 224b of the LEC. This locks expansion wedge 242 in place and prevents the expansion wedge 242 from deforming and buckling outward during expansion and thereafter. The side slot 244 and end receiving space 252 also provide a substantially smooth interface between the expansion wedge and exterior of the LEC Once expansion is complete, the driver, screw, nut and LEC insertion tool are removed from the cannula, leaving only the expanded LEC locked in place.

It will be appreciated that the driver in combination with the screw and the expansion wedge provide a means for translating an applied rotational force into a precisely determined linear vector for expanding the halves LEC 218 vertically along the vertical axis of the entire spine, rather than uniformly (that is, without increasing diameter, which would take up more space inside the vertebral body surfaces).

Referring to FIGS. 5, 6A, and 6B, multiple rows of corrugations or frictional engagement surfaces 238 extend along the longitudinal axis of each LEC half 218a, 218b. Multiple rows of corrugations or frictional engagement surfaces provide external protuberances or bone engaging ridges on the surface of each LEC half 218a, 218b. This effectively maximizes the surface area of the LEC that remains in contact with the bone.

The LEC halves 218a, 218b are expanded vertically in a linear direction in accordance with the rotation of the driver 240 and screw 246. The precise linear height can be directly determined by the rotation of the driver or by the use of an expansion wedge of a known size and angle. The expansion process presses the LEC halves 218a, 218b, strongly into the predrilled vertebral bone grooves 216, thereby securing the adjacent vertebrae to enhance stability during arthrodesis (fusion) healing.

Slots or apertures 254 in FIGS. 6A and 6B are provided through the exterior surface and extend into the interior of each LEC half 218a, 218b. The slots 254 act as sites for internal bone graft material egress, and increase contact areas between the internal bone graft material and the external boney prepared endplates.

It will be appreciated that the maximized surface area of corrugations or bone-engaging surfaces are provided with the series of apertures 254 which provide channels for bone ingrowth. Thus, the surface area for communicating bone graft material from the interior of the LEC to the bone is effectively increased, and the LEC provides a maximized surface area of bone fixation as compared to conventional devices utilizing smooth or threaded surfaces. The effectively maximized surface area also increases avenues for feed through of bone growth enhancing agents in the cylinder to facilitate bone fusion and ingrowth into the LEC with resulting fixation forces greater than adjacent bone and soft tissue failure forces.

An additional advantage of the multiple rows of bone engaging surfaces or corrugations 238 is to provide a maximized surface area of enhanced bone fusion for a minimal sized implant. Thus, bone engaging surfaces of LEC 218 can be provided with a coating such as hydroxyapatite, bone morphogenic protein and or certain enzyme substances that have the propensity to enable bone osteo-inductive and osteo-conductive principles for better healing responses. Alternatively, such morphogenic proteins and enzyme substances for promoting bone growth are advantageously contained in the hollow interior of LEC 218. These substances communicate with the bone-engaging surfaces through the slots 254 that act as conduits for bone in growth. The LEC and its slots 254 are also designed to permit suture free fusion. The slots 254 provide apertures and curvature angles in the areas intended for bone egress between the interior bone graft or bone substitute products, and the outer vertebral bone interface (the interface between vertebral segments 202a, 202b and bone engagement surfaces of LEC 218) involved in the fusion process can be used by a surgeon to pull the interspinal ligament, or other structures through the LEC, thus creating an intentional immediate interface or padding to avert interspinal nerve injuries.

Since the LEC is inserted in a closed or non-expanded state, its interior may advantageously contain bone graft material, bone growth enhancing agents, medication or other agents that promote healing. During the expansion process the expansion wedge 242 progressively moves forward along the sides of the LEC as previously explained. This advantageously keeps the sides of the LEC substantially sealed while simultaneously allowing the LEC to expand in a vertical direction. Thus, medication and bone graft enhancing material contained within the interior of the LEC remain therein during the expansion process.

As the exterior of the LEC presses into the adjacent bone by the force of vertical expansion, the slots provide egress zones for absorption of bone growth enhancers, such as bone morphogenic proteins or other enzyme substances contained within the interior of the LEC. The slots 254 also provide areas for bone in growth thus promoting stable healing. As healing advances, pullout forces are greater than vertebral body failure forces, and patients can mobilize more quickly. Once healing (fusion or arthrodesis) does occur, the implants become incorporated and their role becomes quiescent.

Figure 9:
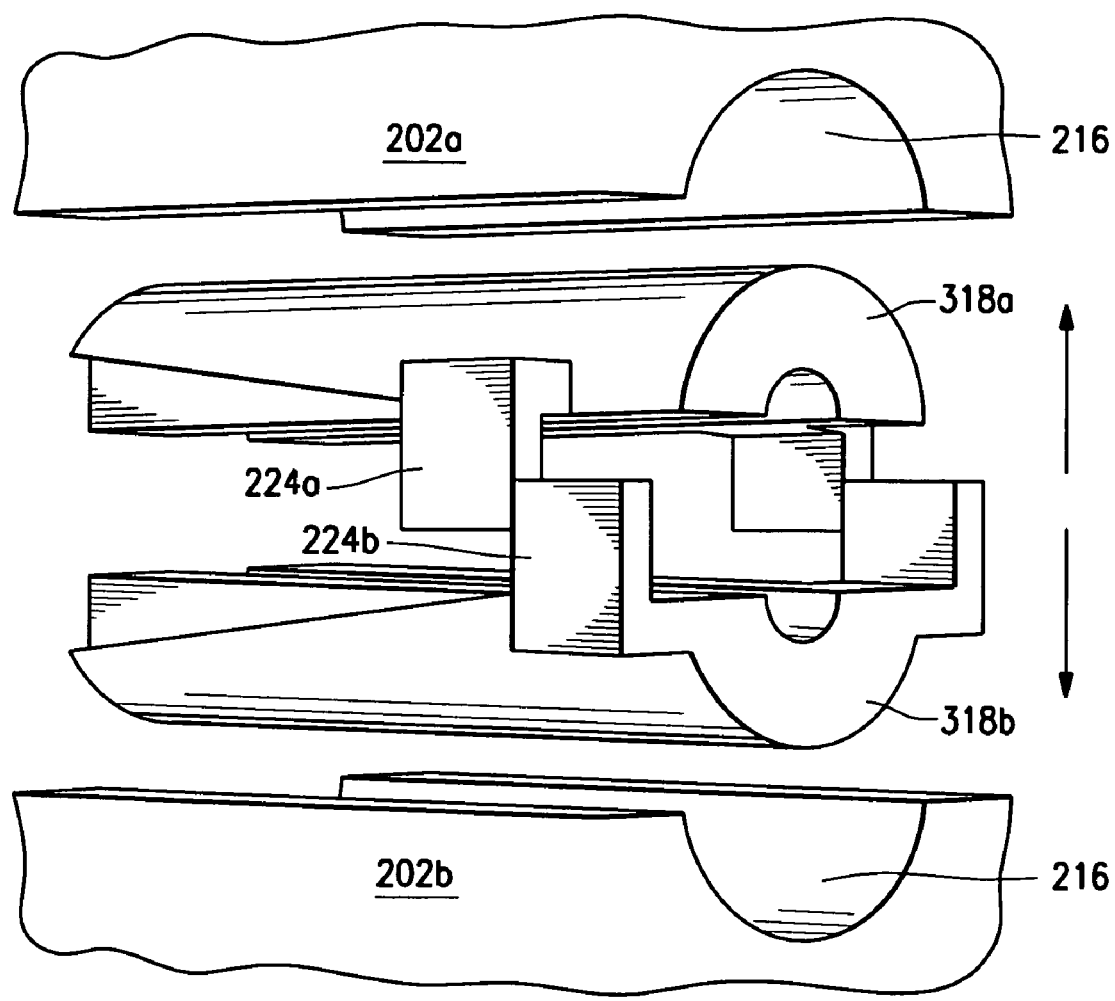
FIG. 9 is a stylized view of the LEC showing linear expansion into corresponding grooves in bone according to an aspect of the invention.

FIG. 9 is a representation showing the LEC being expanded. The LEC halves 318a, 318b expand linearly to a height 30-40 percent greater than the original diameter of the LEC. The height increases to hold the vertebrae 202a, 202b while the width remains stable so as to decrease impingement upon a second cage, or upon neural elements or soft tissue structures in the immediate vicinity. It is understood that the top and bottom surfaces of LEC halves 318a and 318b are in contact with and fit conformably into the congruent surfaces of groove 216 provided in the vertebrae 202a, 202b since the radius of the unexpanded LEC is substantially the same as the radius of the cutting tool that formed groove 216.

When the expansion is at a maximum, that is, the LEC is in the fully expanded state, the driver, in combination with the screw, are removed through the insertion tool and the insertion tool is detached from the cage. U shaped expansion wedge 242 has been drawn all the way into its end receiving space 252 in the interior of the LEC and locks the cage in its linearly expanded position.

Once detached from the insertion tool, the expanded LEC is securely set in groove 216 between two vertebral bodies 202a, 202b. Since the force of fixation is greater than the bone failure strengths, early patient mobilization after surgery is feasible. Force to failure will be approximately 4000 Newtons.

Figure 10A:
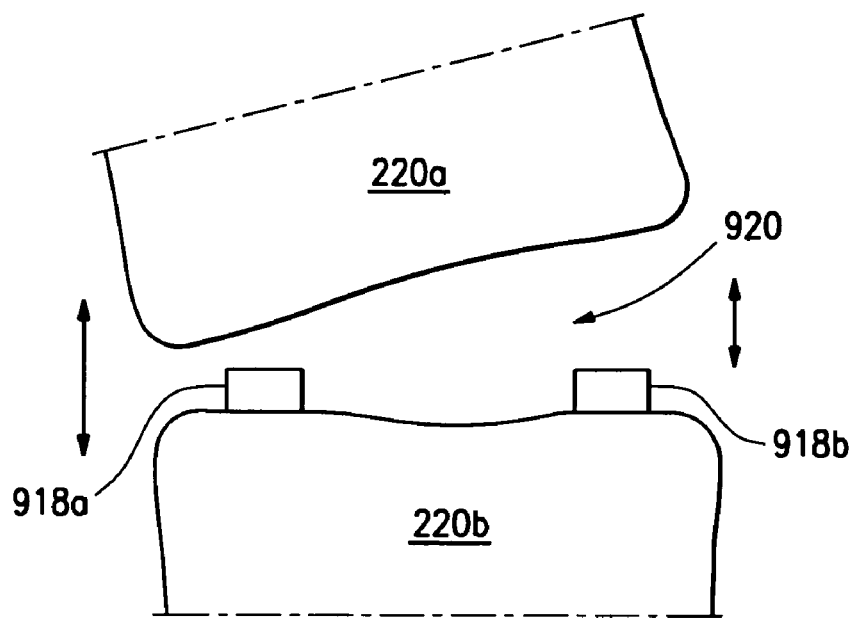
FIG. 10A is a stylized cross-sectional view of the placement of two LECs between vertebral structures for adjustment of spinal alignment according to an aspect of the invention.
Figure 10B:
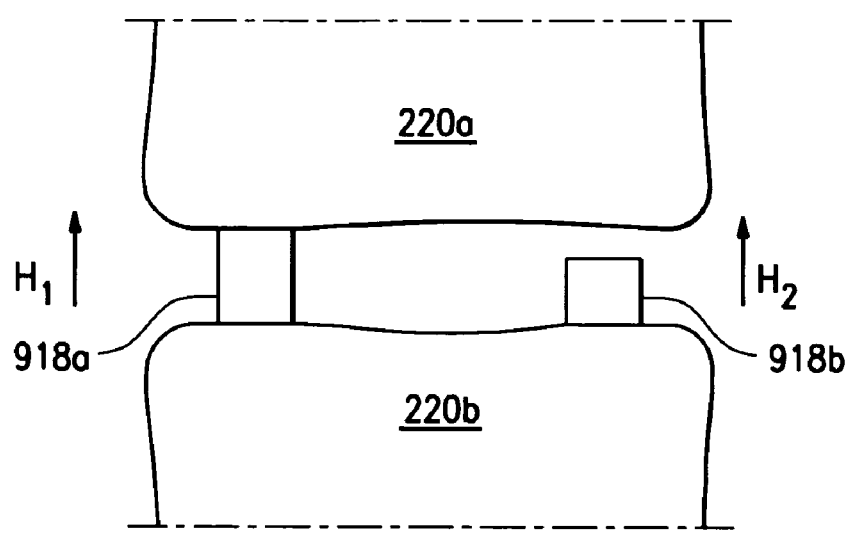
FIG. 10B is a stylized cross-sectional view of the vertical expansion of a first LEC relative to a second LEC for adjustment of spinal alignment according to an aspect of the invention.

Referring to FIGS. 10A and 10B, generally, two LECs 918a, 918b are used for fusion through an anterior approach, though the surgeon can use any insertional vector including a posterior approach. LECs 918a, 918b may be inserted in parallel or obliquely to accommodate located anatomy and to adjust deformities such as scoliosis, kyphosis, and spondylolisthesis. Typically, two LECs 918a, 918b are provided, one on each end of a vertebral body or endplate 220b in an intervertebral space 920. This enables linear expansion into vertebral endplates 220a, 220b which enhances fixation. By increasing fixation forces, earlier mobilization of the patient is encouraged, reducing the need for multiple fixation operations, and all associated risks (anesthesia, surgery complications) are decreased.

The LEC enables selective adjustment of spinal alignment. Due to the known angulation and height of the sides of the expansion wedge, and known radius of the driver and screw, it is possible to expand either LEC 918a or 918b vertically and linearly to a predetermined height $H_1$, $H_2$.

Referring to FIG. 10A, angular correction can be made for scoliosis by elevating or expanding either the medial or lateral side of the cage by dialing in or adjusting an amount of expansion to correct a problem with the natural spine angulation as noted on an AP (anterior/posterior) X ray plane. This adjustment is accomplished by selecting particular sized or expansion wedges as they relate to the cage recipient site. Once the expansion wedge is contained inside the cage, during intraoperative assembly, a preplanned selected cant or angular variation from pure linear expansion is realized. The amount of selected cant is calculated to coordinate with the scoliotic curve, so as to facilitate realignment toward normal For correction of lordosis (as seen on a lateral X-ray view, naturally noted in both the lumbar and cervical regions of the spine), the LEC (anterior cage) can be expanded so that it widens or expands more anterior linearly symmetrically than posterior, thus creating a trapezoidal construct that fills in the disc space more naturally, both expanding into the vertebral endplates, and filling the normally wider anterior space in such a manner that the "flat back syndrome" is eliminated. This promotes fusion in a normal or physiologic alignment.

Referring to FIGS. 10A and 10B, the shape of the linear expansion can be selected or dialed in depending on a selection by the surgeon before or during surgery to adjust alignment so as to: (a) maintain or correct for lumbar lordosis, thereby avoiding the "flat back syndrome"; (b) create more physiologic right or left bending angles to deal with scoliosis in complex reconstruction or salvage cases; (c) fill perceived or actual gaps in spinal bone encountered during surgery such as induced by trauma or by osteo-porotic collapse.

It will be appreciated that due to the placement of the two LECs, one on each side of a vertebral body, it is now possible to adjust spinal alignment as shown in FIG. 10B by expanding a first LEC 918a to a greater predetermined height $H_1$ necessary to bring the two vertebral endplates 220a and 220b into normal alignment. The ability to linearly expand each spine cage to a predetermined height with improved stability and substantially immediate fixation makes it now possible to impart normal lordosis to a spinal column.

The present LEC enables three dimensional correction of spinal malalignments, and maintenance of natural curvatures. Thus, the present LEC may provide a cure for scoliosis or other forms of spinal misalignment. Structural interbody support of the anterior column of the spine has clear biomechanical and clinical benefits compared with conventional posterior/lateral arthodesis. Biomechanically, interbody support improves the stability of the anterior column of the spine and permits load sharing with the region of the spinal motion segment that is exposed to highest loads improving stiffness and reducing rates of implant failure.

Clinically, interbody structural support enhances the rate of successful arthrodesis and is associated with improved clinical outcomes. The present LEC may be placed from an anterior approach to the spine or from a posterior or transforaminal approach. The posterior or transforaminal approach is popular because it permits circumferencial arthrodesis of the spine in a single surgery, eliminating the morbidity of a separate anterior approach. Currently, anterior only surgery is unreliable due to inadequate initial stabilization of the spinal motion segment. With a linearly expandable cage such as the present LEC and consequent rigid interbody fixation, the need for posterior augmentation is advantageously eliminated. Since the LEC expands into the vertebrae with greater fixation forces, the requirements for additional stabilization procedures will be reduced. By starting with a smaller fusion cage, such as the LEC, the surgeon can better approach the destination with less tissue dissection and consequently less injury to nerve roots and soft tissues around the spine.

Figure 10C:
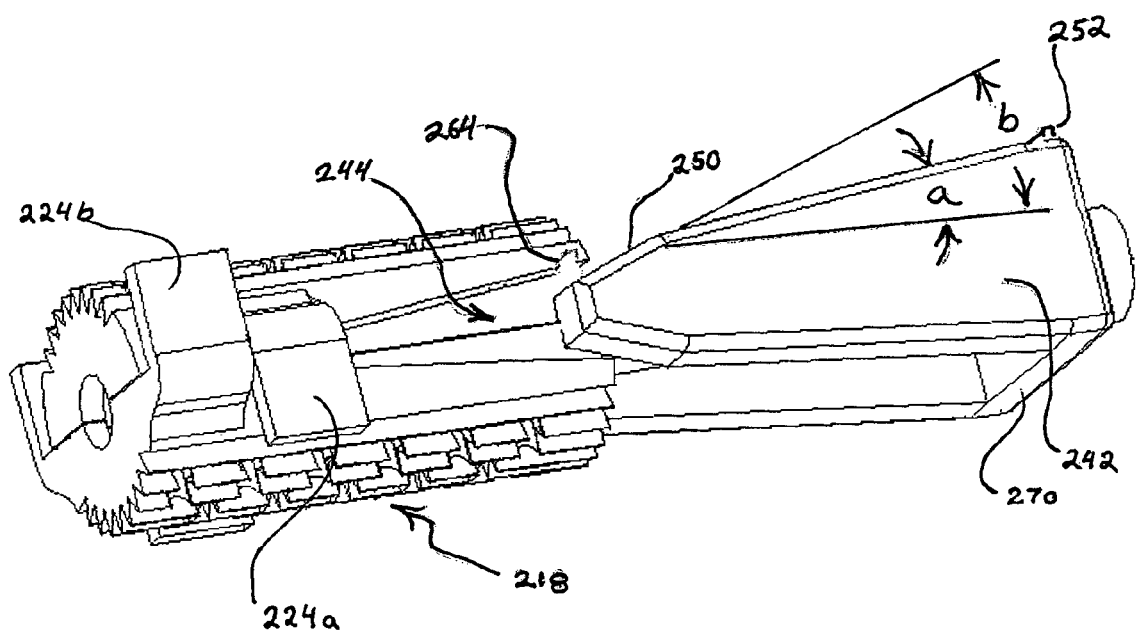
FIG. 10C is perspective view showing how the angle of the expansion wedge in the LEC can be selected to impart varying degrees of expansion to the LEC for a full range of adjustment of spinal alignment according to an aspect of the invention.

Referring to FIG. 10C, it will be appreciated that the present linearly expandable cage 218 provides options for achieving total lordosis correction. This is achieved by using an assortment of pre selected expansion elements 242 wherein wedge shaped angled surface 250 (referred to here as a wedge for clarity) is characterized by an angle such as, for example a, b, or any convenient angle, for imparting a desired lordotic curvature. A physician imparts a desired lordotic curvature by simply selecting different wedges characterized by different sizes and angles, such as angle a or b as shown.

As the expansion element 242 is drawn into receiving slot 244 during the expansion process, the angle and height of the wedge 250 determines the angle of correction and the fully extended height of expansion of cage 218. The final extent of expansion of the cage occurs when expansion lock 262 (a projection provided on the distal end of the wedge 250) slides into engagement with and is locked in place by a corresponding recess 264 provided in the surface of the cage 218 that defines the end of travel for the wedge in the receiving slot 244. It will be appreciated that two corresponding sets of projections 262 and corresponding recesses 264 are provided on the upper and lower surfaces of the wedge and receiving slot for locking engagement to strongly lock the cage in position in its fully expanded state. Only one set is shown for clarity The advantages of inserting two parallel cages as shown in FIGS. 10A and 10B over a single cage are: ease of access/ability to differentially distract in the medial/lateral plane. Selecting various sizes and angles for the sides of the expansion wedge enable predetermined expansion of the LEC halves linearly and vertically; either symmetrically vertically or offset vertically when wedge sides vary in angulation. This enables the LEC to be linear in one plane and either parallel and oblong or trapezoidal in another plane.

Expansion wedges 242 could be chosen to have angled surfaces 250, such as angle a or b in FIG. 10C, that correspond to 4 mm increments as follows: 0 degrees; 4 degrees for providing 0-8 degrees of correction, then wedge angles of 0 degrees and 12 degrees. This would provide total lordosis options of 0, 4, 8, 12, 16, 20 and 28 degrees.

It is advantageous to have an assortment of heights and angles for the expansion wedge. This enables a physician to pre select, before surgery, a desired reconstructive change size to be implanted in a vertebrae in accordance with actual size vertebral segments shown in X rays. The base 270 of the expansion wedge 242 should be 3 mm thick, assuming a 20 mm long cage, since lordotic endplates are 3 mm posterior dimension and anterior height=4.4 mm (=tan(wedge angle)/(20+(3/tan(wedge angle)). Expansion wedges should be available in 2 mm height increments.

In accordance with an aspect of the invention the foregoing features now make it possible to expand a 10 mm spine cage to 20 mm (more commonly to between 10 and 17 mm), while correcting trapezoidally for lordosis, kyphosis or even scoliosis requirements. The foregoing flexibility—the ability to predetermine height of expansion and degree of spinal correction by pre selecting expansion wedges having different sizes and angles, and inserting two expansion wedges in parallel provides an anatomically correct range of spinal correction in three dimensions.

An important advantage of the expandable cage is that the device permits a posterior (single stage) operation to create the lordosis that may normally require a combined anterior and posterior approach. The anterior-based linear cage may permit a single stage surgery if a physician adds a permanent staple to the position of the cannula set screws to provide tension anteriorly. The reason that stand-alone anterior cages are inadequate and require posterior support is that the approach disrupts the anterior tension band (the anterior longitudinal ligament and disc annulus).

By stapling across the implant vertically it is possible to create an anterior plate or tension band that will reconstitute the anterior column stability in extension, enabling a physician to avoid a posterior approach. These staples (two in parallel in vertical orientation) can be placed in the position of the prongs from the insertion canula.

While the invention has been described in connection with what are presently considered to be the most practical and preferred embodiments, it is to be understood that the invention is not limited to the disclosed embodiments and alternatives as set forth above, but on the contrary is intended to cover various modifications and equivalent arrangements included within the scope of the following claims.

For example, equivalent fixation features can be provided for stabilizing the cage within the bone. Other configurations for the overlapping wing portions of the LEC halves may be utilized to provide interlocking capability and maintain linear expansion.

Also, other compositions of additives, such as various types of biogenic materials for enhancing bone growth can be added to the interior portion of the LEC. Other materials for construction of the LEC may be substituted for Titanium without departing from the scope of the invention.

As one skilled in the art will readily appreciate from the disclosure of the present invention, processes, machines, compositions of matter, methods, or steps, presently existing or later to be developed that perform substantially the same function or achieve substantially the same result as the corresponding embodiments described herein may be utilized according to the present invention. Therefore, persons of ordinary skill in this field are to understand that all such equivalent processes, arrangements and modifications are to be included within the scope of the following claims.

I claim:

1. A spinal implant system comprising a pair of linearly, expanding spine cages (LEC) for insertion through cannulas along axes of insertion in a pair of radial grooves cut in the bone of adjacent first and second vertebral bodies and for providing immediate fixation and stabilization thereof, each of the expanding spine cages comprising;

a first half cylindrical shell having a radial surface for conformable engagement in the groove cut in the first vertebral body and having an angled surface on each side thereof, a second half cylindrical shell, complementary with respect to the first half cylindrical shell, having a radial surface for conformable engagement in the groove cut in the second vertebral body and having an angled surface on each side thereof, the first and second cylindrical shells being joined in an unexpanded state along a longitudinal axis in common with the axis of insertion, such that the half cylindrical shells define a cylinder with an interior space for holding a quantity of bone growth enhancing agents and the angled surfaces on the first and second half cylindrical shells forming an angled slot, expansion alignment structures at each of the matching ends of the first and second half cylindrical shells to maintain alignment during expansion, and the radius of the cylinder in its unexpanded state is less than the radius of the cannula and substantially equal to the radial groove cut in the vertebral bodies; and expansion means for expanding the first and second cylindrical shells linearly and orthogonally to the axis of insertion while maintaining constant fixation between the radial surfaces and conformably engaged vertebral bodies, the expansion means comprising expansion wedges which slidably fit into the angled slots formed by the angled surfaces of the first and second cylindrical shells.

2. The spinal implant system of claim 1 wherein the first and second radial surfaces of each spine cage further comprise multiple rows of corrugations or bone engaging ridges extending in parallel long the longitudinal axis of each LEC half to provide maximized surface area for bone engagement and fixation.

3. The spinal implant system of claim 1 wherein the first and second radial surfaces of each spine cage further comprise a multiplicity of radially extending pointed surface projections that provide a maximized surface area for bone engagement and fixation.

4. The spinal implant system of claim 1 wherein the first and second radial surfaces of each spine cage are provided with a plurality of slots or through holes for maximized feed through of bone growth enhancing agents contained in the interior of each of the LEC to facilitate bone ingrowth through the slots for enhanced bone fixation, such that fixation forces are greater than adjacent bone and soft tissue failure forces.

5. The spinal implant system of claim 1 wherein the expansion means for each spine cage further comprises a U shaped expansion wedge comprising first and second angled sides joined by a base, the angled sides adapted for advancement between the two halves of each of the LEC upon application of force to the base, such that advancement each of the wedges expands the LEC halves linearly in accordance with the angle imparted by the wedge, while bone engaging surfaces remain fixed.

6. The spinal implant system of claim 5 wherein height and angle of expansion of each of the LEC's are predetermined by selecting an expansion wedge having sides of a desired height and angle to provide a complete range of spinal correction.

7. The spinal implant system of claim 5 wherein the first and second angled sides of the wedge correspond at least in part to the angled surfaces on the first and second half cylindrical shells forming the angled slot which receives the wedge.

8. The spinal implant system of claim 1 wherein height and angle of expansion of each of the LEG's are determined during expansion by selecting an amount the expansion wedges fits into the angled slots.

9. A spine cage linearly expandable between adjacent vertebral segments in a vertical direction, the spine cage characterized in its non-expanded state by a minimized longitudinal radius substantially equal to the radius of a cutting head for minimally invasive insertion in a radial groove cut by the cutting head in first and second adjacent vertebral segments comprising:

a first half cylinder comprising a radial surface including a plurality of corrugations or rows of bone engaging projections for increasing surface area and enhancing fixation with the corresponding radial cut in the first vertebral segment, and having a pair of sidewalls extending tangentially from each side of the radial surface, with a portion of each sidewall defining a first angled surface; and a second half cylinder comprising a radial surface including a plurality of corrugations or rows of bone engaging projections for increasing surface area and enhancing fixation with the corresponding radial cut in the second vertebral segment and having a pair of sidewalls extending tangentially from each side of the radial surface, defining a second angled surface, such that the first and second angled surfaces form an angled slot on each side of the cage;

expansion alignment structures at matching ends of the first and second half cylindrical shells to maintain alignment during expansion, and an expansion means comprising first and second angled wedges joined by a base, the wedges being adapted for slidable advancement into the slot, such that upon application of force to the base, the wedges move forward in the slot, expanding the first and second halves in a desired linear direction according to the angle and height of each wedge, while facilitating locking engagement between the radial surfaces and adjacent vertebral segments by force from expansion of each radial surface with a corresponding vertebral body.

10. A linearly expanding spine cage as in claim 9, wherein bone engaging surfaces of the spine cage are provided with a coating selected from the group consisting of hydroxyapatite, bone morphogenic protein and enzyme substances that have the propensity to enable bone osteo-inductive and osteo-conductive effects for an improved healing response.

11. A linearly expanding spine cage (LEC) for insertion adjacent first and second vertebral bodies and for providing immediate fixation and stabilization thereof comprising;

a first half cylindrical shell having a radial surface for engagement of the first vertebral body and having an angled surface on each side thereof, a second half cylindrical shell, complementary with respect to the first half cylindrical shell, having a radial surface for engagement of the second vertebral body and having an angled surface on each side thereof, the first and second cylindrical shells being joined in an unexpanded state along a longitudinal axis, such that the half cylindrical shells define a cylinder with an interior space for holding a quantity of bone growth enhancing agents and the angled surfaces on the first and second half cylindrical shells forming angled slots, expansion alignment structures at the matching ends of the first and second cylindrical shells to maintain alignment during expansion, and expansion means for expanding the first and second cylindrical shells linearly and orthogonally to the longitudinal axis while maintaining constant fixation between the radial surfaces and engaged vertebral bodies, the expansion means comprising expansion wedges which slidably fit longitudinally axis into the angled slots wherein an amount of fit between the expansion wedges and the first and second cylindrical shells is variable and user selectable such that the amount of linear expansion is user selectable.

12. The linearly expanding spine cage of claim 11 wherein the amount of fit is configured to provide a linear expansion of the LEC between 0 and about 10 mm.

13. The linearly expanding spine cage of claim 11 wherein the expansion wedges have angled sides of between 0.5 and 12 degrees.

14. The linearly expanding spine cage of claim 11 wherein the expansion is only substantially orthogonal such that the tops of the radial surfaces for engagement of the first and second vertebral body are parallel in the unexpanded state but angled in the expanded state.

* * * * *

UNITED STATES PATENT AND TRADEMARK OFFICE
CERTIFICATE OF CORRECTION

| | | |
|---|---|---|
| PATENT NO. | : 7,722,674 B1 | Page 1 of 1 |
| APPLICATION NO. | : 11/202725 | |
| DATED | : May 25, 2010 | |
| INVENTOR(S) | : R. Thomas Grotz | |

It is certified that error appears in the above-identified patent and that said Letters Patent is hereby corrected as shown below:

In column 14, claim 8, line 49, delete "LEG's" and insert --LEC's-- therefore;

In column 16, claim 11, line 19, delete "axis".

Signed and Sealed this
Twenty-second Day of March, 2011

David J. Kappos
*Director of the United States Patent and Trademark Office*